US012648691B2

(12) United States Patent
Hakoshima

(10) Patent No.: US 12,648,691 B2
(45) Date of Patent: Jun. 9, 2026

(54) DISTANCE CALCULATION DEVICE, DISTANCE CALCULATION METHOD, AND DISTANCE CALCULATION PROGRAM

(71) Applicant: JVCKENWOOD Corporation, Yokohama (JP)

(72) Inventor: Shuji Hakoshima, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 505 days.

(21) Appl. No.: 18/105,907

(22) Filed: Feb. 6, 2023

(65) Prior Publication Data

US 2023/0181034 A1 Jun. 15, 2023

Related U.S. Application Data

(63) Continuation of application No. PCT/JP2021/008895, filed on Mar. 8, 2021.

(30) Foreign Application Priority Data

Aug. 20, 2020 (JP) ................................. 2020-139307

(51) Int. Cl.
*A61B 3/11* (2006.01)
*A61B 3/00* (2006.01)
*A61B 3/14* (2006.01)
(52) U.S. Cl.
CPC ............ *A61B 3/111* (2013.01); *A61B 3/0025* (2013.01); *A61B 3/14* (2013.01)
(58) Field of Classification Search
CPC ......... A61B 3/111; A61B 3/0025; A61B 3/14; A61B 3/113; A61B 3/11; A61B 3/00;

(Continued)

(56) References Cited

U.S. PATENT DOCUMENTS

| | | | | |
|---|---|---|---|---|
| 5,835,190 A | * | 11/1998 | Miyake .................. | A61B 3/107 351/212 |
| 2011/0109880 A1 | * | 5/2011 | Nummela .......... | G02B 27/0081 351/210 |

(Continued)

FOREIGN PATENT DOCUMENTS

| | | |
|---|---|---|
| EP | 0821908 | 2/1998 |
| JP | 10-73662 | 3/1998 |

(Continued)

OTHER PUBLICATIONS

English translation of JP-2018128749 (Aug. 16, 2018).*

(Continued)

*Primary Examiner* — Thomas K Pham
*Assistant Examiner* — Kuei-Jen L Edenfield
(74) *Attorney, Agent, or Firm* — Amin, Turocy & Watson, LLP

(57) ABSTRACT

A distance calculation device includes a first light source and a second light source that emit detection light from positions different from each other and that apply the detection light to at least one of eyeballs of a subject; an imaging unit that captures an image of the eyeball of the subject to which the detection light is applied; a position calculator that, based on the image of the eyeball of the subject that is captured by the imaging unit, calculates each of a position of a first cornea reflection center according to the detection light from the first light source and a position of a second cornea reflection center according to the detection light from the second light source; a center-center distance calculator that calculates a center-center distance between the position of the first cornea reflection center and the second cornea reflection center; and an object distance calculator.

4 Claims, 11 Drawing Sheets

(58) Field of Classification Search
CPC ...... A61B 3/107; G06V 10/25; G06V 10/141;
G06V 40/165; G06V 40/18; G06V
40/193; G06V 40/16; G01B 11/026;
G01B 11/02; G06F 3/013; G06F 3/01
USPC ................................................ 351/204–221
See application file for complete search history.

(56) References Cited

U.S. PATENT DOCUMENTS

| | | | | |
|---|---|---|---|---|
| 2018/0042477 | A1* | 2/2018 | Seitz ...................... | A61B 3/152 |
| 2023/0181033 | A1* | 6/2023 | Hakoshima .............. | A61B 3/14 |
| | | | | 351/206 |

FOREIGN PATENT DOCUMENTS

| | | | |
|---|---|---|---|
| JP | 4649319 | | 3/2011 |
| JP | 2011115460 | A * | 6/2011 |
| JP | 2018128749 | A * | 8/2018 |

OTHER PUBLICATIONS

English translation of JP2011115460 (Jun. 16, 2011).*
International Search Report and Written Opinion for International
Application No. PCT/JP2021/008895 mailed on May 18, 2021, 8
pages.

* cited by examiner $$\left\{\begin{array}{l} \theta 1 = \dfrac{1}{2} \cdot arctan\left(\dfrac{a}{x}\right) \\[2mm] \theta 2 = \dfrac{1}{2} \cdot arctan\left(\dfrac{b}{x}\right) \\[2mm] d = r \cdot sin\theta 1 + r \cdot sin\theta 2 \end{array}\right.$$

DISTANCE CALCULATION DEVICE, DISTANCE CALCULATION METHOD, AND DISTANCE CALCULATION PROGRAM

CROSS-REFERENCE TO RELATED APPLICATION(S)

This application is a Continuation of PCT international application Ser. No. PCT/JP2021/008895 filed on Mar. 8, 2021 which designates the United States, incorporated herein by reference, and which claims the benefit of priority from Japanese Patent Application No. 2020-139307, filed on Aug. 20, 2020, incorporated herein by reference.

BACKGROUND OF THE INVENTION

1. Technical Field

The present disclosure relates to a distance calculation device, a distance calculation method, and a distance calculation program.

2. Description of the Related Art

A line-of-sight detection device that, by a plurality of light sources, emits detection light and applies the detection light to an eyeball of a subject, by a single imaging unit, acquires an image of the eyeball to which the detection light is applied, and detects a direction of the line of sight of the subject based on the acquired image and the distance between the imaging unit and the subject has been known (for example, see Japanese Patent No. 4649319).

In the line-of-sight detection device described above, a system using an ultrasound sensor, a system using a stereo camera, a system of finding from a position of a lens on which a camera makes a focus, or the like, is used in order to detect a distance between the imaging unit and the subject. Each of these systems however makes the configuration complicated.

SUMMARY

A distance calculation device according to the present disclosure comprising: a first light source and a second light source that emit detection light from positions different from each other and that apply the detection light to at least one of eyeballs of a subject; an imaging unit that captures an image of the eyeball of the subject to which the detection light is applied; a position calculator that, based on the image of the eyeball of the subject that is captured by the imaging unit, calculates each of a position of a first cornea reflection center according to the detection light from the first light source and a position of a second cornea reflection center according to the detection light from the second light source; a center distance calculator that calculates a center-center distance between the position of the first cornea reflection center and the second cornea reflection center; and an object distance calculator that, based on the center-center distance and a cornea curvature radius of the eyeball of the subject, calculates an object distance between the imaging unit and the eyeball of the subject.

A distance calculation method according to the present disclosure comprising: emitting detection light from a first light source and a second light source that are arranged in positions different from each other and applying the detection light to at least one of eyeballs of a subject; by an imaging unit, capturing an image of the eyeball of the subject to which the detection light is applied; based on the captured image of the eyeball of the subject, calculating each of a position of a first cornea reflection center according to the detection light from the first light source and a position of a second cornea reflection center according to the detection light from the second light source; calculating a center-center distance between the first cornea reflection center and the second cornea reflection center; and based on the center-center distance and a cornea curvature radius of the eyeball of the subject, calculating an object distance between the imaging unit and the eyeball of the subject.

A non-transitory computer readable recording medium storing therein a distance calculation program according to the present disclosure that causes a computer to execute a process of emitting detection light from a first light source and a second light source that are arranged in positions different from each other and applying the detection light to at least one of eyeballs of a subject; a process of, by an imaging unit, capturing an image of the eyeball of the subject to which the detection light is applied; a process of, based on the captured image of the eyeball of the subject, calculating each of a position of a first cornea reflection center according to the detection light from the first light source and a position of a second cornea reflection center according to the detection light from the second light source; a process of calculating a center-center distance between the first cornea reflection center and the second cornea reflection center; and a process of, based on the center-center distance and a cornea curvature radius of the eyeball of the subject, calculating an object distance between the imaging unit and the eyeball of the subject.

Advantageous Effects of Invention

According to the disclosure, it is possible to calculate a distance between an imaging unit and a subject by a simple configuration.

DETAILED DESCRIPTION OF THE PREFERRED EMBODIMENTS

An embodiment of the disclosure will be described below based on the drawings. The embodiment does not limit the invention. The components in the embodiment described below include ones easily replaceable by those skilled in the art or ones substantially the same.

In the following description, description on a positional relationship among components will be given, setting a three-dimensional global coordinate system. A direction parallel to a first axis on a given plane is set for a X-axis direction, a direction parallel to a second axis on a given plane orthogonal to the first axis is set for a Y-axis direction, and a direction parallel to a third axis orthogonal to each of the first axis and the second axis is set for a Z-axis direction. The given planes include an X-Y plane.

Cornea Curvature Radius Calculation Device and Line-of-Sight Detection Device

Figure 1:
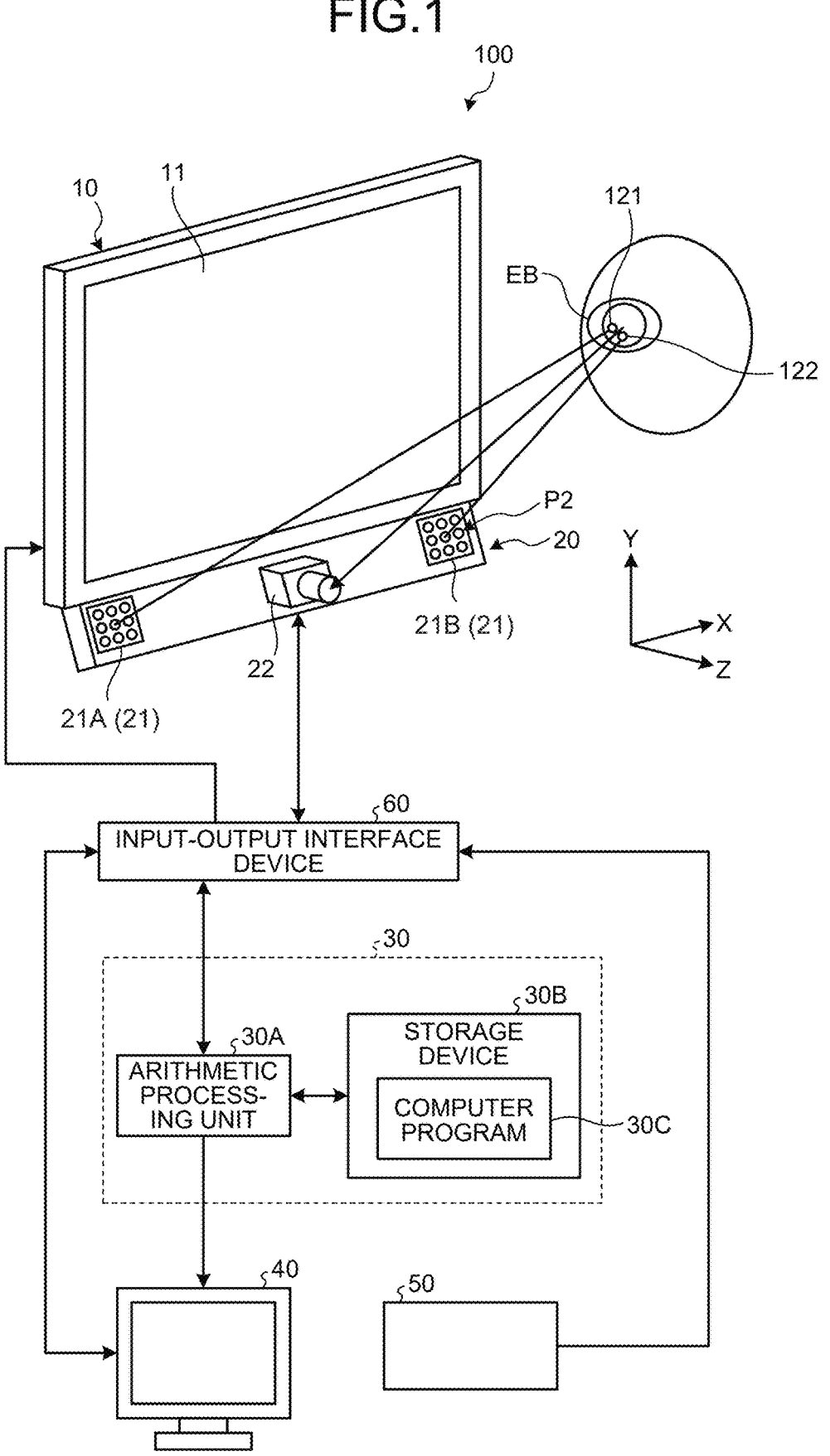
FIG. 1 is a diagram schematically illustrating an example of a line-of-sight detection device according to an embodiment.

FIG. 1 is a diagram schematically illustrating an example of a line-of-sight detection device 100 according to the embodiment. The line-of-sight detection device 100 according to the embodiment detects lines of sight of a subject and outputs a detection result. The line-of-sight detection device 100 detects a line of sight, for example, based on a position of a pupil of the subject and a position of a cornea reflection image.

As illustrated in FIG. 1, the line-of-sight detection device 100 includes a display device 10, an image acquisition device 20, a computer system 30, an output device 40, an input device 50, and an input-output interface device 60. The display device 10, the image acquisition device 20, the computer system 30, the output device 40, and the input device 50 perform data communications via the input-output interface device 60. Each of the display device 10 and the image acquisition device 20 includes a drive circuit not illustrated in the drawing.

The display device 10 includes a flat panel display, such as a liquid crystal display (LCD) or an organic electroluminescence display (OLED). In the embodiment, the display device 10 includes a display unit 11. The display unit 11 displays information, such as an image. The display unit 11 is substantially parallel to the X-Y plane. The X-axis direction is a left-right direction of the display unit 11, the Y-axis direction is an up-down direction of the display unit 11, and the Z-axis direction is a depth direction orthogonal to the display unit 11. The display device 10 may be a head mounted display device. In the case of a head-mounted display, such a configuration as that of the image acquisition device 20 is arranged in a head mounted module.

The image acquisition device 20 acquires image data on left and right eye balls EB of the subject and transmits the acquired image data to the computer system 30. The image acquisition device 20 includes a light source unit 21 and an imaging unit 22.

The light source unit 21 emits detection light to the eyeball EB of the subject. The light source unit 21 includes a first light source 21A and a second light source 21B that are arranged in positions different from each other. The first light source 21A and the second light source 21B contain LED (light emitting diode) light sources and are able to emit near-infrared light of, for example, a wavelength of 850 [nm]. The first light source 21A and the second light source 21B are able to control the timing of emission of the detection light.

The imaging unit 22 acquires image data by capturing images of the left and right eyeballs EB of the subject. In the embodiment, the single imaging unit 22 is provided. Various cameras corresponding to a method of detecting a line of sight of the subject are used as the imaging unit 22. As in the embodiment, in the case of a system that detects a line of sight based on a position of a pupil of a subject and a position of a corneal reflection image, the imaging unit 22 includes an infrared camera and includes an optical system that can transmit near-infrared light of a wavelength of, for example, 850 [nm] and an imaging device capable of receiving the near-infrared light. The imaging unit 22 outputs a frame synchronization signal. The period of the frame synchronization signal can be set at, for example, 20 [msec]; however, the period is not limited to this. In the embodiment, the imaging unit 22 is a single camera. The imaging unit 22 is arranged in a middle position between the first light source 21A and the second light source 21B. The image data that is acquired by the imaging unit 22 has a configuration in which pixels having luminances that are set by 8-bit values (0 to 255) are arrayed two-dimensionally. The luminance presents that, the smaller the value is, the darker it is and, the larger the value is, the brighter it is. A pixel whose value of luminance is 0 is displayed as black in the image data. A pixel whose value of luminance is 255 is displayed as white in the image data.

The computer system 30 has general control on operations of the line-of-sight detection device 100. The computer system 30 includes an arithmetic processing unit 30A and a storage device 30B. The arithmetic processing unit 30A includes a microprocessor, such as a CPU (central processing unit). The storage device 30B includes memories, such as a ROM (read only memory) and a RAM (random access memory), or a storage. The arithmetic processing unit 30A performs arithmetic processing according to a computer program 30C that is stored in the storage device 30B.

The output device 40 includes a display device, such as a flat panel display. Note that the output device 40 may include a printing device. The input device 50 generates input data by being operated. The input device 50 includes a keyboard or a mouse for computer systems. Note that the input device 50 may include a touch sensor with which the display unit of the output device 40 serving as a display device is provided.

The line-of-sight detection device 100 according to the embodiment is a device in which the display device 10 and the computer system 30 are independent from each other. Note that the display device 10 and the computer system 30 may be integrated. For example, the line-of-sight detection device 100 may include a tablet personal computer. In this case, a display device, an image acquisition device, a computer system, an input device, an output device, etc., may be installed in the tablet personal computer.

Figure 2:
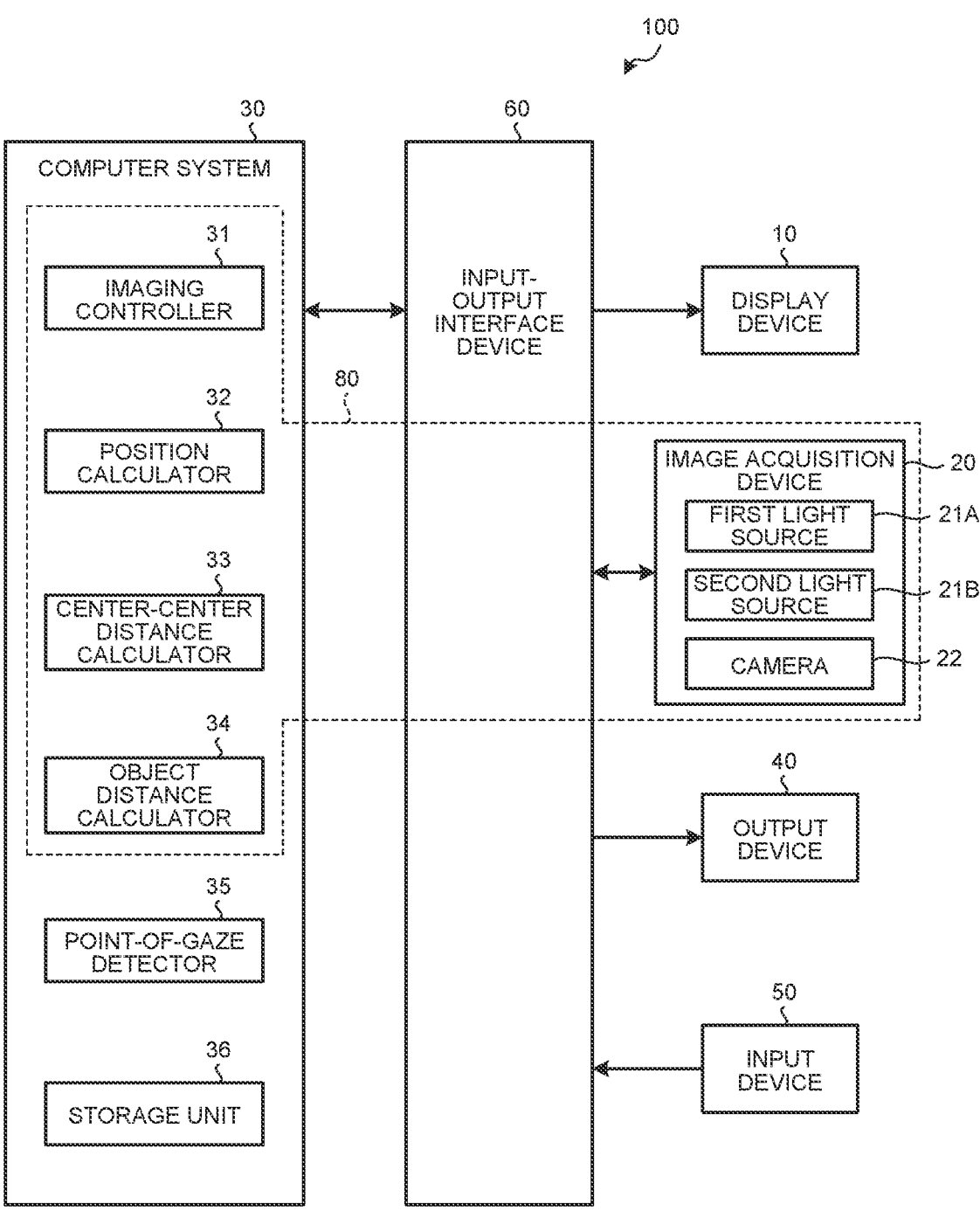
FIG. 2 is a functional block diagram illustrating an example of the line-of-sight detection device.

FIG. 2 is a functional block diagram illustrating an example of the line-of-sight detection device 100. As illustrated in FIG. 2, the computer system 30 includes an imaging controller 31, a position calculator 32, a center-center distance calculator 33, an object distance calculator 34, a detection processor 35, and a storage unit 36. Functions of the computer system 30 are implemented by the arithmetic processing unit 30A and the storage device 30B (refer to FIG. 1). Part of the functions of the computer system 30 may be provided outside the line-of-sight detection device 100. In the embodiment, a distance calculation device 80 consists of the light source unit 21 (the first light source 21A and the second light source 21B) and the imaging unit 22 of the image acquisition device 20, the imaging controller 31, the position calculator 32, the center-center distance calculator 33, and the object distance calculator 34. The distance calculation device 80 may include at least one of the detection processor 35 and the storage unit 36.

The imaging controller 31 controls the light source unit 21 and the imaging unit 22. The imaging controller 31 controls the timing of emission of the detection light, the time of emission, etc., with respect to each of the first light source 21A and the second light source 21B. The imaging controller 31 controls the timing of imaging, etc., with respect to the imaging unit 22. The imaging controller 31 causes the detection light to be emitted from the first light source 21A and the second light source 21B in synchronization with the period of the frame synchronization signal of the imaging unit 22. In the embodiment, the imaging controller 31 causes the first light source 21A and the second light source 21B to emit the detection light alternately, for example, in every period of the frame synchronization signal. The imaging controller 31 acquires image data that is acquired by the image acquisition device 20. The imaging controller 31 stores the acquired image data in the storage unit 36.

Based on the image data on the eyeballs of the subject that is captured by the imaging unit 22, the position calculator 32 calculates each of a position of a first cornea reflection center 121 (refer to FIG. 1 and FIG. 3) according to the detection light from the first light source 21A and a position of a second cornea reflection center 122 (refer to FIG. 1 and FIG. 3) according to the detection light from the second light source 21B. The first cornea reflection center 121 and the second cornea reflection center 122 are centers of cornea reflection images (a first cornea reflection image 120A and a second cornea reflection image 120B) according to the respective sets of the detection light. The position calculator 32 stores the calculated positions of the first cornea reflection center 121 and the second cornea reflection center 122 in the storage unit 36.

The center-center distance calculator 33 calculates a center-center distance between the position of the first cornea reflection center 121 and the second cornea reflection center 122.

Based on the center-center distance and a cornea curvature radius of the eyeball of the subject, the object distance calculator 34 calculates an object distance between the imaging unit 22 and the eyeball EB of the subject. The object distance calculator 34 stores the calculated object distance in the storage unit 36. The object distance calculator 34 is able to set a given constant for the cornea curvature radius of the eyeball of the subject and calculate an object distance. The cornea curvature radius is a distance between the surface of the cornea of the eyeball EB and the cornea curvature center. The cornea curvature radius and the cornea curvature center will be described below.

Based on the image data that is captured by the imaging unit 22 and the object distance, the detection processor 35 calculates a position of the cornea curvature center of the eyeball of the subject. Based on the image data, the detection processor 35 detects a position of the pupil center of the subject. The pupil center is the center of a pupil 112. Based on the calculated position of the pupil center and the positions of the first cornea reflection center 121 and the second cornea reflection center 122 that are calculated by the position calculator 32, the detection processor 35 calculates a position of the cornea curvature center of the eyeball EB.

An overview of a process of calculating a position of the cornea curvature center in the detection processor 35 will be described. In the embodiment, the case in which the eyeballs EB are illuminated with the first light source 21A and the second light source 21B and the single imaging unit 22 captures images of the eyeballs EB is described. Note that there is no limitation to the case with the single imaging unit and the same description applies also to the case with a single light source and two cameras.

Figure 3:
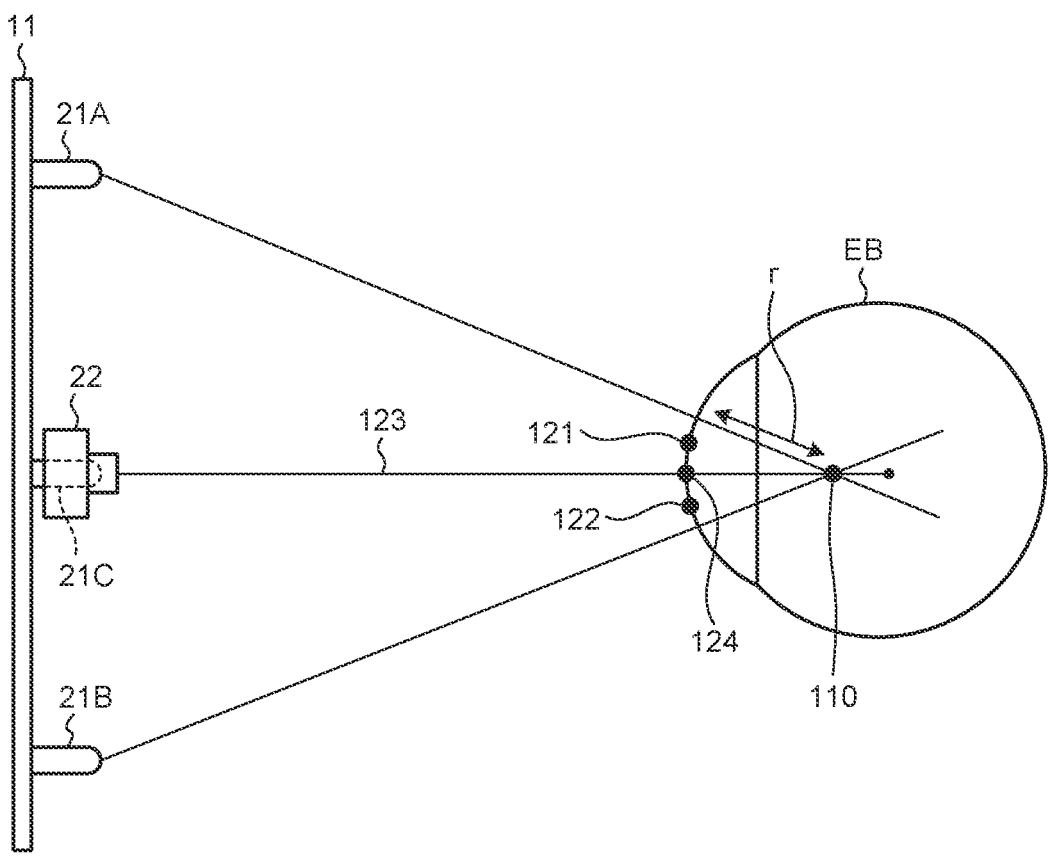
FIG. 3 is a diagram schematically illustrating a state in which detection light from a light source unit is applied to an eyeball of a subject.

FIG. 3 is a diagram schematically illustrating a state in which the detection light from the light source unit 21 is applied to the eyeballs EB of the subject. As illustrated in FIG. 3, in the embodiment, the first light source 21A and the second light source 21B of the light source unit 21 are arranged in positions that are symmetrical with respect to the imaging unit 22. Thus, in this case, it can be regarded that a virtual light source 21C is in the position of the imaging unit 22.

The first cornea reflection center 121 represents a corneal reflection center in an image in the case where the detection light is applied to the eyeball EB from the first light source 21A. The second cornea reflection center 122 represents a cornea reflection center in an image in the case where the detection light is applied to the eyeball EB from the second light source 21B. A cornea reflection center 124 represents a cornea reflection center corresponding to the virtual light source 21C.

The position of the cornea reflection center 124 is calculated based on the positions of the first cornea reflection center 121 and the second cornea reflection center 122. The detection processor 35 calculates a position of the imaging unit 22 on the image with respect to the first cornea reflection center 121 and the second cornea reflection center 122. Based on the object distance between the imaging unit 22 and the eyeball EB of the subject, the detection processor 35 transforms the position into a three-dimensional coordinate system. A transformation parameter for transforming a position into a three-dimensional coordinate system is stored in, for example, the storage unit 36. Based on the positions of the first cornea reflection center 121 and the second cornea reflection center 122 that are determined by the three-dimensional coordinate system, the detection processor 35 calculates a position of the cornea reflection center 124 in the three-dimensional coordinate system.

A cornea curvature center 110 is on a straight line 123 connecting the virtual light source 21C and the cornea reflection center 124. The detection processor 35 calculates, as a position of the cornea curvature center 110, a position in which the distance from the cornea reflection center 124 is a given value on the straight line 123. A cornea curvature radius r is used as the given value. The cornea curvature radius r is the distance between the surface of the cornea and the cornea curvature center 110. For example, a constant that is determined previously based on a general cornea curvature radius value can be used as a value of the cornea curvature radius r. The value of the cornea curvature radius r is used also in, for example, the object distance calculator 34 described above.

The detection processor 35 detects a line-of-sight vector of each of the left and right eyeballs EB of the subject based on the positon of the pupil center and the position of the cornea curvature center. After detecting the line-of-sight vector, the detection processor 35 detects a position of a point of gaze representing the intersection between the line-of-sight vector and the display unit 11.

The storage unit 36 stores various types of data and programs for performing processing in each unit of the computer system 30. The storage unit 36 stores, for example, data on an image to be displayed on the display unit 11. The storage unit 36 stores each of the image data that is acquired by the imaging controller 31, the positions of the first cornea reflection center 121 and the second cornea reflection center 122 that are calculated by the position calculator 32, the object distance that is calculated by the object distance calculator 34, and the cornea curvature radius r that is detected by the detection processor 35.

The storage unit 36 also stores a cornea curvature radius calculation program that causes a computer to execute a process of emitting detection light from the first light source 21A and the second light source 21B that are arranged in the positions different from each other and applying the detection light to at least one of the eyeballs EB of a subject; a process of, by the imaging unit 22, capturing an image of the eyeball EB of the subject to which the detection light is applied; a process of, based on the captured image of the eyeball of the subject, calculating each of a position of the first cornea reflection center 121 according to the detection light from the first light source 21A and a position of the second cornea reflection center 122 according to the detection light from the second light source 21B; a process of calculating a center-center distance between the positon of the first cornea reflection center 121 and the second cornea reflection center 122; and a process of calculating an object distance between the imaging unit 22 and the eyeball EB of the subject based on the center-center distance and the cornea curvature radius r of the eyeball of the subject.

Distance Calculation Method

Figure 4:
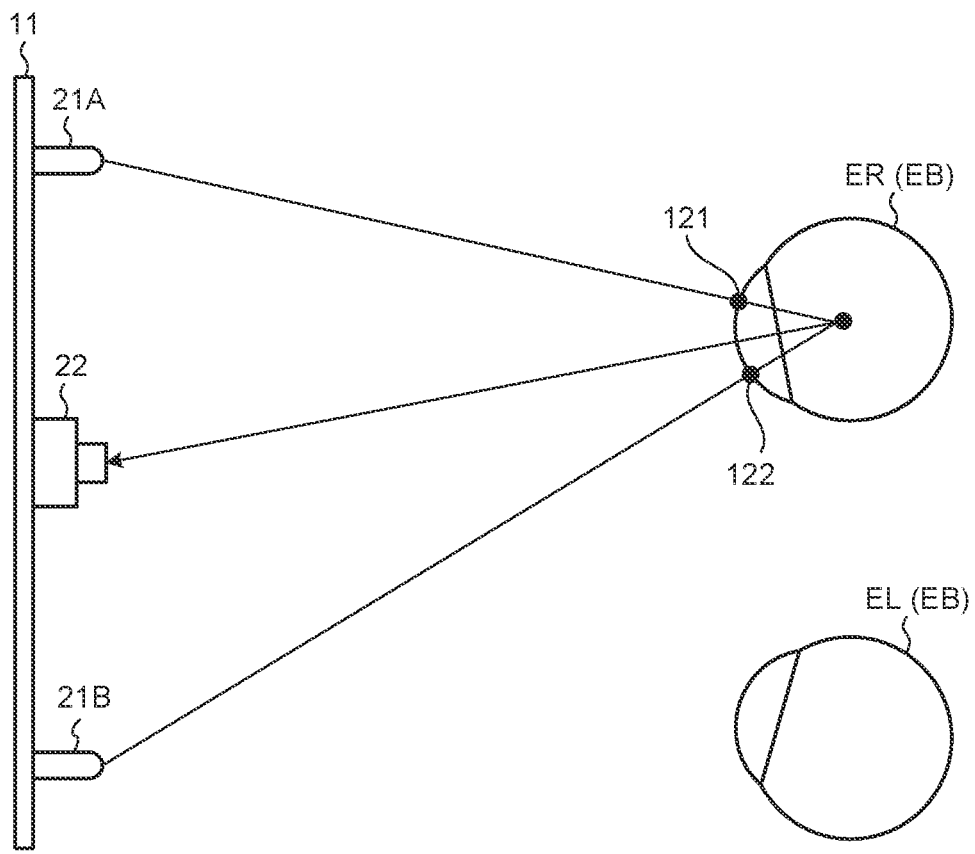
FIG. 4 is a diagram schematically illustrating schematically illustrating a state in which detection light from the light source unit is applied to the eyeball of the subject.
Figure 5:
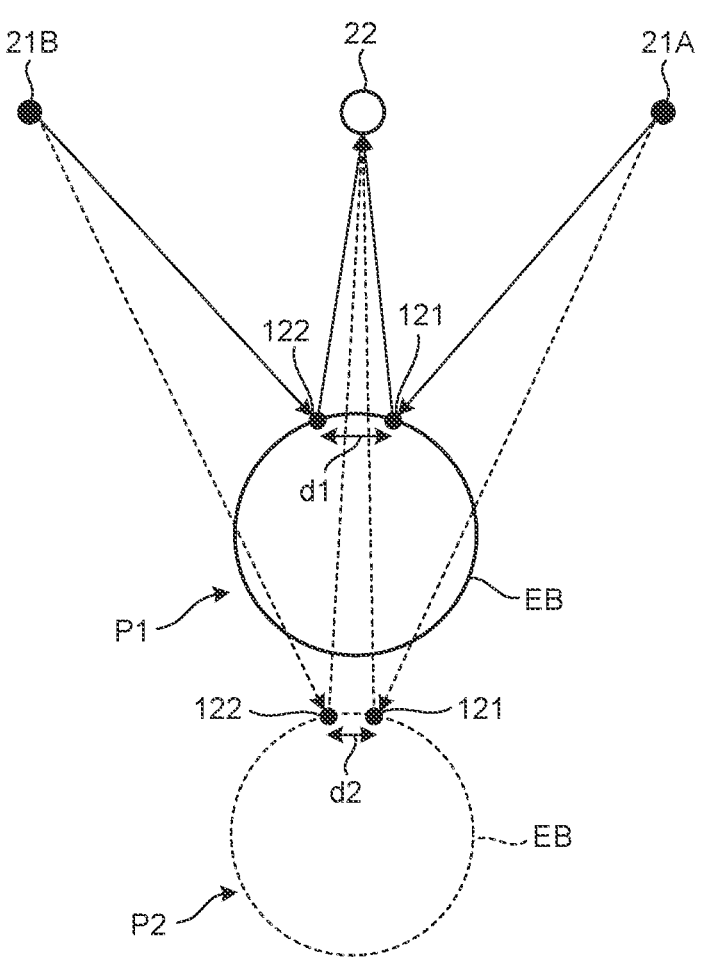
FIG. 5 is a diagram schematically illustrating a state in which the detection light from the light source unit is applied to the eyeball of the subject.

A distance calculation method according to the embodiment will be described next. FIG. 4 and FIG. 5 are diagrams schematically illustrating the state in which the detection light from the light source unit 21 is applied to the eyeball EB of the subject. The eyeball EB of the subject on the right (the right eyeball ER) will be described below and the eyeball EB on the left (the left eyeball EL) can be described similarly. As illustrated in FIG. 4 and FIG. 5, when the detection light is applied from the first light source 21A and the second light source 21B, a cornea reflection image is formed on the cornea of the eyeball EB. The center of the cornea reflection image of the first light source 21A is the first cornea reflection center 121. The center of the cornea reflection image of the second light source 21B is the second cornea reflection center 122.

As illustrated in FIG. 5, in association with variation in the distance between the imaging unit 22 and the subject, a center-center distance d between the first cornea reflection center 121 and the second cornea reflection center 122 varies. For example, d1>d2 holds when a camera-subject distance d1 in the case where the object distance that is the distance between the imaging unit 22 and the eyeball EB of the subject is x1 (a position P1) and a center-center distance d2 in the case where the object distance is x2 larger than x1 (a position P2).

Figure 6:
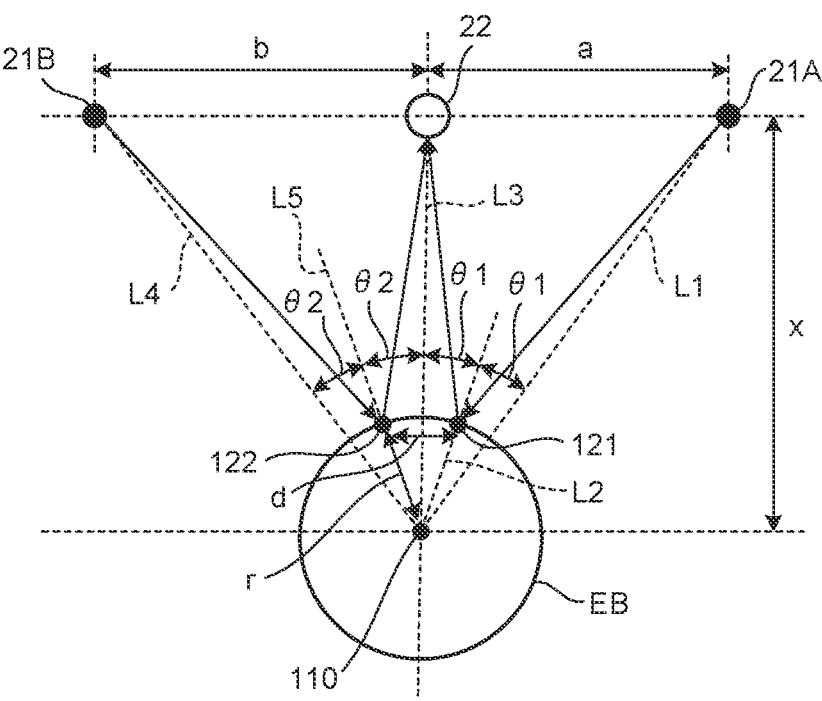
FIG. 6 is a diagram illustrating an example of a positional relationship of the light source unit, an imaging unit, and the eyeball of the subject.

FIG. 6 is a diagram illustrating an example of a positional relationship of the light source unit, the imaging unit, and the eyeball of the subject. As illustrated in FIG. 6, a distance between the first light source 21A and the imaging unit 22 is referred to as a, a distance between the second light source 21B and the imaging unit 22 is referred to as b, an object distance between the imaging unit 22 and the subject is referred to as x, a distance between the cornea reflection center 121 and the cornea reflection center 122 that are detected in the eyeball EB is referred to as d, and a cornea curvature radius is referred to as r. In this example, the object distance x is a distance between the imaging unit 22 and the cornea curvature center 110 of the eyeball EB of the subject. Here, because r<<x, it is possible to make an approximation of equality between an angle formed by a straight line L1 passing through the cornea curvature center 110 and the first light source 21A and a straight line L2 passing through the cornea curvature center 110 and the cornea reflection center 121 and an angle formed by a straight line L3 passing through the cornea curvature center 110 and the imaging unit 22 and the straight line 2. The angle is referred to as θ1 below. Similarly, it is possible to make an approximation of equality between an angle formed by a straight line L4 passing through the cornea curvature center 110 and the second light source 21B and a straight line L5 passing through the cornea curvature center 110 and the cornea reflection center 121 and an angle formed by the straight line L3 passing through the cornea curvature center 110 and the imaging unit 22 and the straight line 5. The angle is referred to as θ2 below.

In this case, Equation 1 holds from Equation 3.

$$\theta1 = \arctan(a/x)/2 \qquad \text{(Equation 1)}$$

$$\theta2 = \arctan(n/2)/2 \qquad \text{(Equation 2)}$$

$$d = r \cdot \sin\theta1 + r \cdot \sin\theta2 \qquad \text{(Equation 3)}$$

Figure 7:
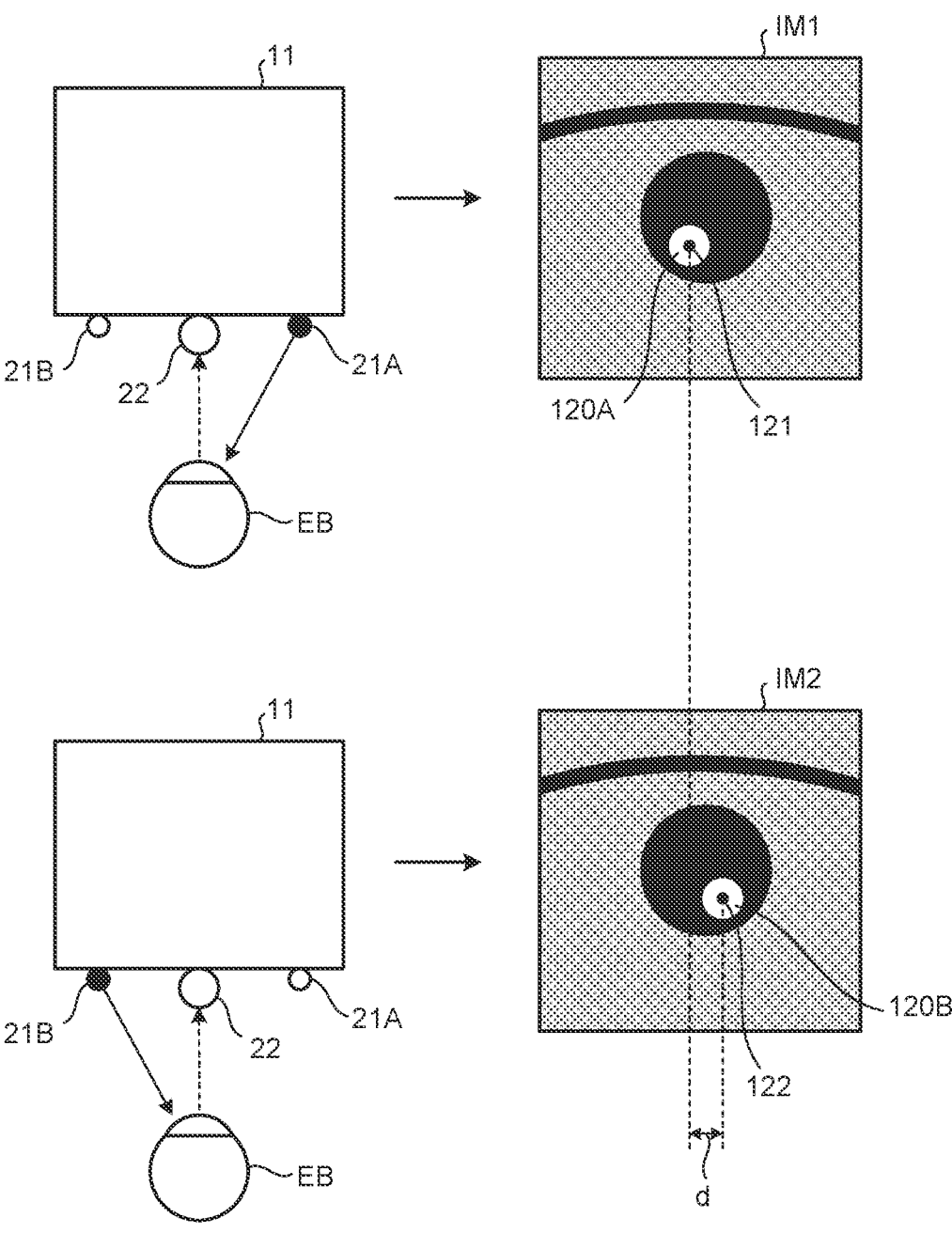
FIG. 7 is a diagram illustrating an example of image data on the eyeball that is captured by the imaging unit.

FIG. 7 is a diagram illustrating an example of the image data on the eyeball EB that is captured by the imaging unit 22. As illustrated in FIG. 7, in the embodiment, image data IM1 in the case where imaging is performed with the detection light from the first light source 21A being applied to the eyeball EB and image data IM2 in the case where imaging is performed with the detection light from the second light source 21B being applied to the eyeball EB are acquired as separate sets of image data. A cornea reflection image according to the detection light from the first light source 21A (referred to as the first cornea reflection image 120A below) appears in the image data IM1. A cornea reflection image according to the detection light from the second light source 21B (referred to as the second cornea reflection image 120B below) appears in the image data IM2. In the embodiment, the first light source 21A and the second light source 21B are turned on at different sets of timing. For this reason, as for appearance of the first cornea reflection image 120A and the second cornea reflection image 120B, only the first cornea reflection image 120A appears in the image data IM1 on one hand and only the second cornea reflection image 120B appears in the image data IM2 on the other hand.

Based on the acquired image data IM1, the position calculator 32 calculates a position of the first cornea reflection center 121 according to the detection light from the first light source 21A. Based on the acquired image data IM2, the position calculator 32 calculates a position of the second cornea reflection center 122 according to the detection light from the second light source 21B. In the sets of image data IM1 and IM2, the pixels from which the first cornea reflection image 120A and the second cornea reflection image 120B have higher luminances than those of other pixels. The position calculator 32 searches for a pixel with the highest luminance in the sets of image data IM1 and IM2, finds a high-luminance area where there are pixels whose luminances are within a given range based on the pixel, finds a luminance gravity center of the area, and sets of coordinates of the luminance gravity centers on the images as the first cornea reflection center 121 and the second cornea reflection center 122. Note that, it is schematically illustrated in FIG. 7 that the luminance of the high luminance area is being uniform; however, for example, the luminance may lower from one pixel in the high luminance area to surrounding pixels.

The center-center distance calculator 33 calculate an actual distance d (mm) between the first cornea reflection center 121 and the second cornea reflection center 122 from a distance (the number of pixels of the imaging device) d' between the first cornea reflection center 121 contained in the image data IM1 and the second cornea reflection center 122 contained in the image data IM2. Note that, in FIG. 7, black points are represented in FIG. 7 in order to easily determine the positions of the first cornea reflection center 121 and the second cornea reflection center 122; however, there is no black point actually.

The following Equation 4 holds when a focal length of a lens configuring the imaging unit 22 is f and a distance between pixels of the imaging device configuring the imaging unit 22 (pitch) is p.

$$d' = (f \cdot d/x)/p \qquad \text{(Equation 4)}$$

Solving Equation 4 about d' from Equation 1 described above leads to $$d' = r \cdot (\sin(\arctan(a/x)/2) + \sin(\arctan(b/x)/2)) \cdot f(p \cdot x). \qquad \text{(Equation 5)}$$

In Equation 5, for example, when a,b=100 (mm), f=12 (mm), r=7.9 (mm), p=0.0048 (mm/pixel), a relation between x and d' like Equation 6 below is found. Note that, in the embodiment, a value (7.9) of the cornea curvature radius r is a given constant. As for the value of the cornea curvature radius r, for example, a value that is determined previously from a value of a general cornea curvature radius may be used or a value that is calculated in a calibration process may be used.

$$d' = 7.9 \cdot (2 \cdot \sin(\arctan(100/x)/2)) \cdot 12/(0.0048 \cdot x) \qquad \text{(Equation 6)}$$

Figure 8:
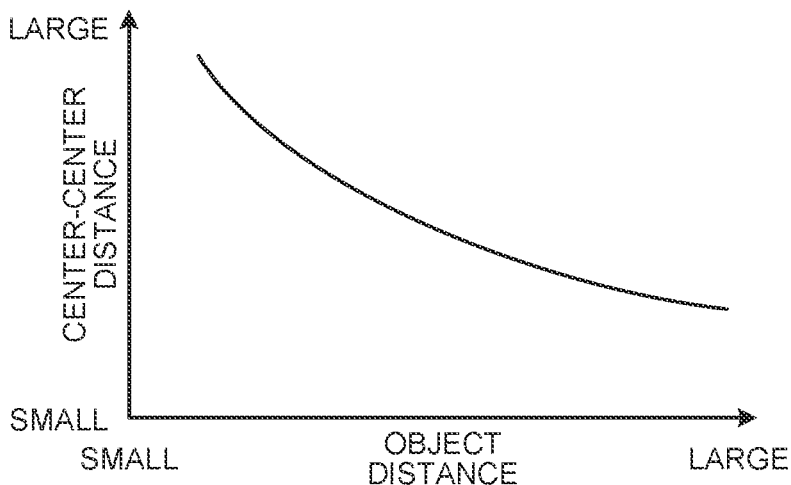
FIG. 8 is a graph illustrating an example of a relation between a center-center distance and an object distance.

Using Equation 6 above makes it possible to calculate an object distance x based on a center-center distance d'. FIG. 8 is a graph illustrating an example of a relation between a center-center distance d' and an object distance x. As for the relation between the enter-center distance d' and the object distance x represented by Equation 6, FIG. 8 presents that, the larger the object distance x is, the smaller the center-center distance d' is.

Line-of-Sight Detection Method

Figure 9:
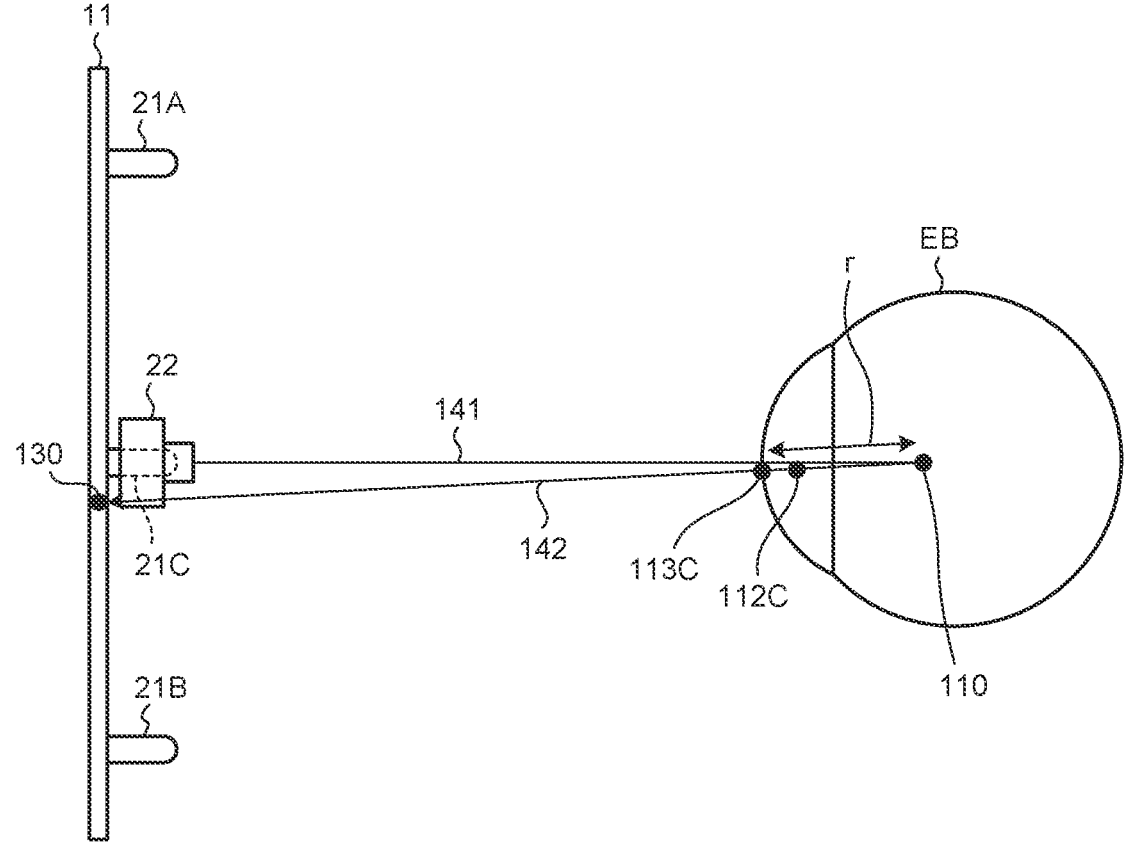
FIG. 9 is a schematic diagram for describing the principle of a calibration process according to the embodiment.

An example of a line-of-sight detection method using the line-of-sight detection device 100 will be described next. In the line-of-sight detection method in the embodiment, after a calibration process is performed, a point-of-gaze detection process is performed. First of all, the principle of the calibration process will be described. FIG. 9 is a schematic diagram for describing the principle of the calibration process according to the embodiment. In the calibration process, a target position 130 is set in order for a subject to have a gaze. The target position 130 is determined in a three-dimensional global coordinate system. In this case, the detection processor 35 displays a target image in the target position 130 that is set.

The first light source 21A and the second light source 21B alternately illuminate the eyeball EB with the detection light. The imaging unit 22 captures an image of the eyeball EB to which the detection light is applied. Based on image data on the eyeball EB, the detection processor 35 detects a position of a pupil center 112C and a positon of a cornea reflection center 113C corresponding to the virtual light source 21C. Using an object distance x that is calculated by the object distance calculator 34, the detection processor 35 converts each of the positions of the pupil center 112C and the cornea reflection center 113C into a global coordinate system.

The detection processor 35 calculates a position of the cornea curvature center 110 based on a position of the virtual light source 21C, a position of the target position 130, the position of the pupil center 112C, and the position of the cornea reflection center 113C. Specifically, the detection processor 35 finds a first straight line 141 connecting the virtual light source 21C and the cornea reflection center 113C. The detection processor 35 finds a second straight line 142 connecting the target position 130 and the pupil center 112C. The detection processor 35 finds the intersection of the first straight line 141 and the second straight line 142 as the position of the cornea curvature center 110. The detection processor 35 calculates a distance between the cornea curvature center 110 and the cornea reflection center 113C as the cornea curvature radius r. The detection processor 35 stores the value of the calculated cornea curvature radius r as calibration data in the storage unit 36.

Figure 10:
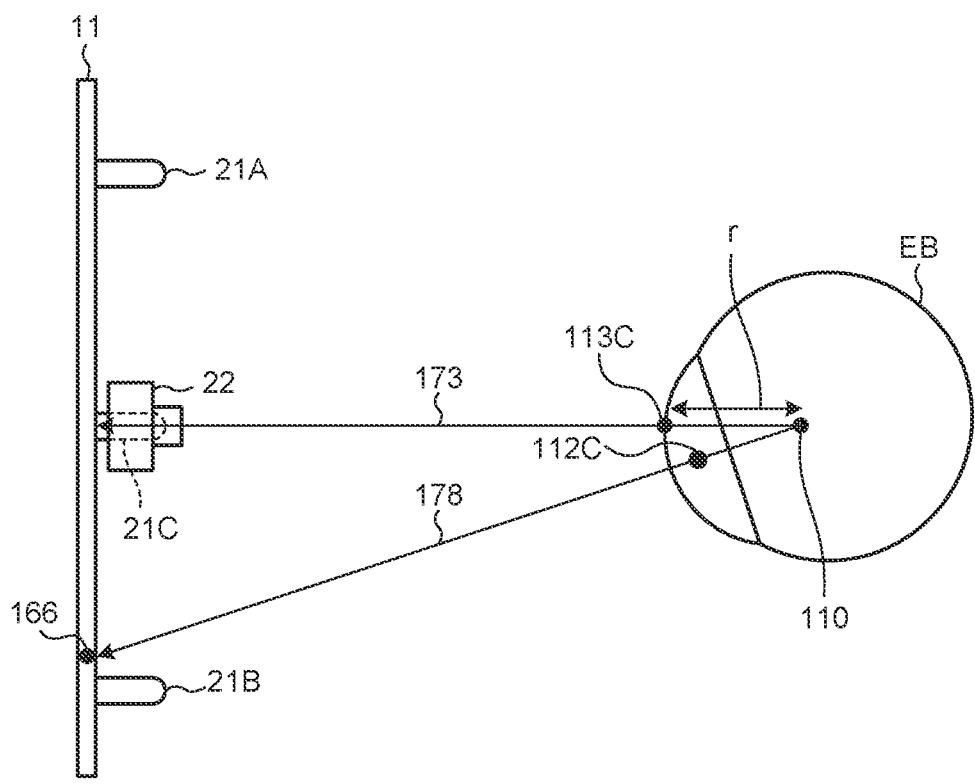
FIG. 10 is a schematic diagram for describing a principle of a line-of-sight detection process according to the embodiment.

The principle of a line-of-sight detection process will be described next. FIG. 10 is a schematic diagram for describing the principle of the line-of-sight detection process according to the embodiment. In the line-of-sight detection process, similarly to the calibration process, the detection light is emitted from the first light source 21A and the second light source 21B alternately and illuminates the eyeball EB and, by the imaging unit 22, an image of the eyeball EB is captured. Based on acquired image data on the eyeball EB, the detection processor 35 detects a position of the pupil center 112C and a positon of the cornea reflection center 113C. Using the object distance x that is calculated by the object distance calculator 34, the detection processor 35 converts each of the positions of the pupil center 112C and the cornea reflection center 113C into a global coordinate system.

The detection processor 35 calculates a position of the cornea curvature center 110 based on the position of the virtual light source 21C, the position of the pupil center 112C, the position of the cornea reflection center 113C, and the cornea curvature radius r that is calculated in the calibration process. Specifically, the detection processor 35 calculates a straight line 173 connecting the virtual light source 21C and the cornea reflection center 113C. The detection processor 35 calculates, as a position of the cornea curvature center 110, a position separated from the cornea reflection center 113C with respect to an inner side of the eyeball EB by a distance corresponding to the cornea curvature radius r. The detection processor 35 calculates a straight line 178 connecting the pupil center 112C and the cornea curvature center 110 and calculates a position of an intersection 166 of the straight line 178 and the display unit 11 as a position of a point of gaze.

Figure 11:
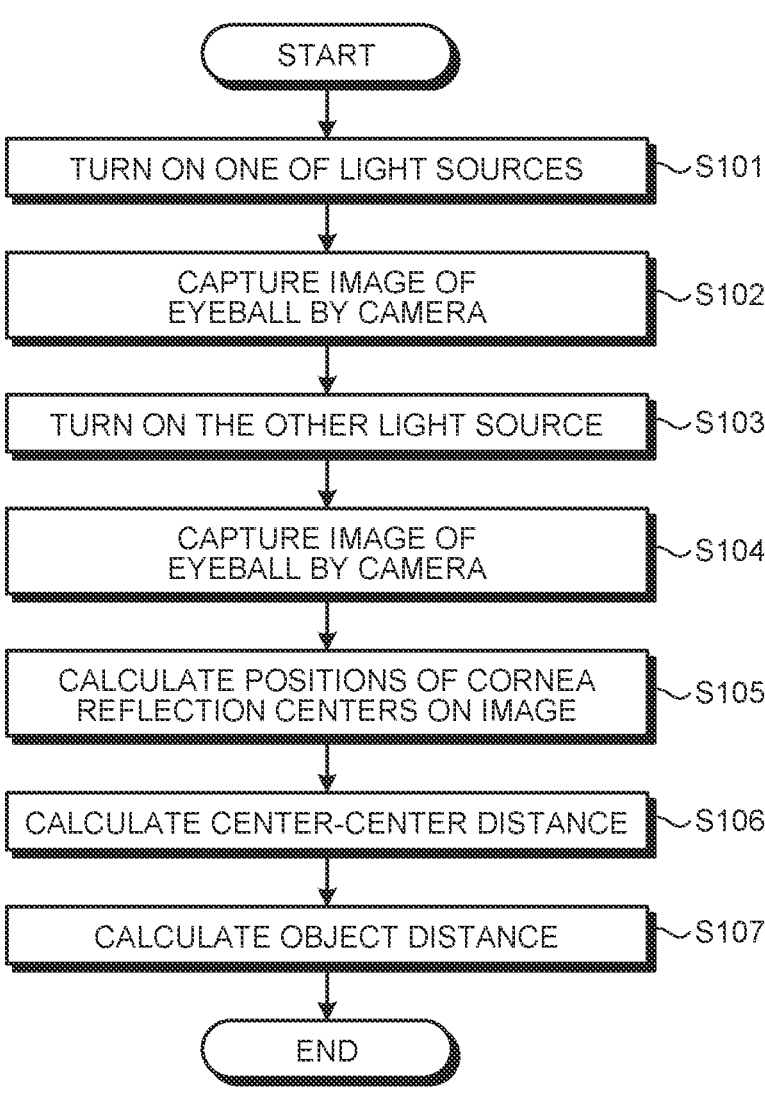
FIG. 11 is a flowchart illustrating an example of a distance calculation method according to the embodiment.

An example of the distance calculation method according to the embodiment will be described next with reference to FIG. 11. FIG. 11 is a flowchart illustrating an example the distance calculation method according to the embodiment. As illustrated in FIG. 11, according to control by the imaging controller 31, one of the first light source 21A and the second light source 21B is caused to emit light and detection light is applied to the eyeball EB (step S101) and, by the imaging unit 22, an image of the eyeball EB of the subject is captured (step S102). According to control by the imaging controller 31, the other one of the first light source 21A, the second light source 21B is caused to emit light and detection light is applied to the eyeball EB (step S103) and, by the imaging unit 22, an image of the eyeball EB of the subject is captured (step S104). The imaging controller 31 acquires image data on the left and right eyeballs EB that is captured by the imaging unit 22.

Based on the acquired image data, the position calculator 32 calculates each of the first cornea reflection center 121 in the first cornea reflection image 120A and the second cornea reflection center 122 in the second cornea reflection image 120 with respect to the right and left eyeballs EB (step S105). The center-center distance calculator 33 calculates a center-center distance d' that is a distance between the first cornea reflection center 121 and the second cornea reflection center 122 (step S106). Based on the calculated center-center distance d', the object distance calculator 34 calculates an object distance x (step S107).

As described above, the distance calculation device 80 according to the embodiment includes the first light source 21A and the second light source 21B that emit detection light from positions different from each other and apply the detection light to at least one of eyeballs EB of a subject; the imaging unit 22 that captures an image of the eyeball EB of the subject to which the detection light is applied; the position calculator 32 that, based on the image of the eyeball EB of the subject that is captured by the imaging unit 22, calculates each of a position of the first cornea reflection center 121 according to the detection light from the first light source 21A and a position of the second cornea reflection center 122 according to the detection light from the second light source 21B; the center-center distance calculator 33 that calculates a center-center distance d' between the position of the first cornea reflection center 121 and the second cornea reflection center 122; and the object distance calculator 34 that, based on the center-center distance d' and the cornea curvature radius r of the eyeball EB of the subject, calculates an object distance between the imaging unit 22 and the eyeball EB of the subject.

The distance calculation method according to the embodiment includes emitting detection light from the first light source 21A and the second light source 21B that are arranged in positions different from each other and applying the detection light to at least one of the eyeballs EB of a subject; by the imaging unit 22, capturing an image of the eyeball EB of the subject to which the detection light is applied; based on the captured image of the eyeball EB of the subject, calculating each of a position of the first cornea reflection center 121 according to the detection light from the first light source 21A and a position of the second cornea reflection center 122 according to the detection light from the second light source 21B; calculating a center-center distance d' between the position of the first cornea reflection center 121 and the second cornea reflection center 122; and, based on the center-center distance d' and the cornea curvature radius r of the eyeball EB of the subject, calculating an object distance between the imaging unit 22 and the eyeball EB of the subject.

The distance calculation program according to the embodiment causes a computer to execute a process of emitting detection light from the first light source 21A and the second light source 21B that are arranged in positions different from each other and applying the detection light to at least one of the eyeballs EB of a subject; a process of, by the imaging unit 22, capturing an image of the eyeball EB of the subject to which the detection light is applied; a process of, based on the captured image of the eyeball EB of the subject, calculating each of a position of the first cornea reflection center 121 according to the detection light from the first light source 21A and a position of the second cornea reflection center 122 according to the detection light from the second light source 21B; a process of calculating a center-center distance d' between the position of the first cornea reflection center 121 and the second cornea reflection center 122; and a process of, based on the center-center distance d' and the cornea curvature radius r of the eyeball EB of the subject, calculating an object distance between the imaging unit 22 and the eyeball EB of the subject.

According to the above-described configuration, the center-center distance d' between the position of the first cornea reflection center 121 and the second cornea reflection center 122 is calculated based on the image data obtained by the imaging unit 22 and, based on the calculated center-center distance d' and the cornea curvature radius r of the eyeball EB of the subject, the object distance between the imaging unit 22 and the eyeball EB of the subject is calculated and thus it is possible to calculate the distance between the imaging unit 22 and the subject without a complicated configuration of an ultrasound sensor, a stereo camera, or the like.

In the distance calculation device 80 according to the embodiment, the first light source 21A and the second light source 21B emit the detection light alternately and the position calculator 32 calculates the position of the first cornea reflection center 121 based on the image that is captured at the timing at which the detection light is emitted from the first light source 21A and calculates the position of the second cornea reflection center 122 based on the image that is captured at the timing at which the detection light is emitted from the second light source 21B. When the detection light is emitted from the first light source 21A and the second light source 21B simultaneously, the first cornea reflection image 120A according to the detection light from the first light source 21A and the second cornea reflection image 120B according to the detection light from the second light source 21B overlap in some cases and there is a possibility that accuracy of detection of the first cornea reflection center 121 and the second cornea reflection center 122 would lower. On the other hand, the above-described configuration makes it possible to acquire the first cornea reflection image 120A and the second cornea reflection image 120B as different images and therefore it is possible to accurately detect the first cornea reflection center 121 and the second cornea reflection center 122.

In the distance calculation device 80, the object distance calculator 34 sets the given constant for the cornea curvature radius r of the eyeball EB of the subject and calculates the object distance x. According to this configuration, because the given constant is set for the cornea curvature radius r of the eyeball EB of the subject, it is possible to calculate the object distance x easily.

The technical scope of the disclosure is not limited to the above-described embodiment and changes can be added as appropriate without departing from the scope of the disclosure. For example, in the above-described embodiment, the case where the first light source 21A and the second light source 21B are caused to turn on is exemplified; however, embodiments are not limited to this and the imaging unit 22 may capture an image with the first light source 21A and the second light source 21B being caused to turn on at the same timing.

Figure 12:
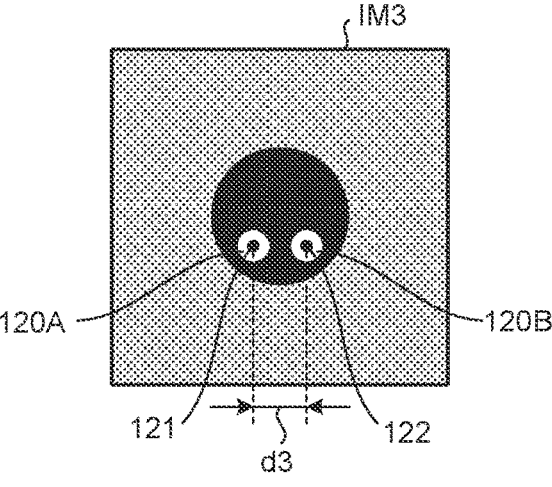
FIG. 12 is a diagram illustrating an example of the image data on the eyeball that is captured with the first light source and the second light source being turned on at the same timing.
Figure 13:
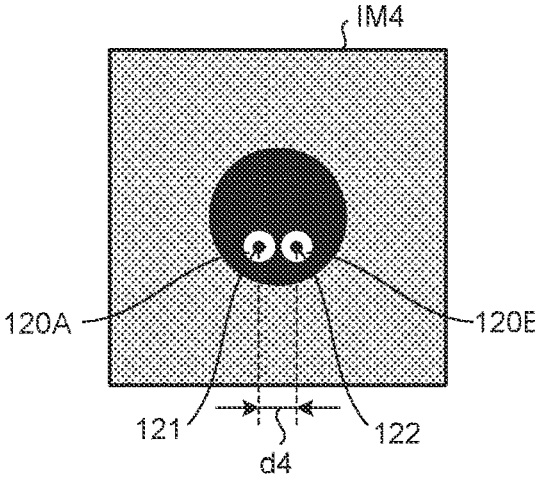
FIG. 13 is a diagram illustrating an example of the image data on the eyeball that is captured with the first light source and the second light source being turned on at the same timing.
Figure 14:
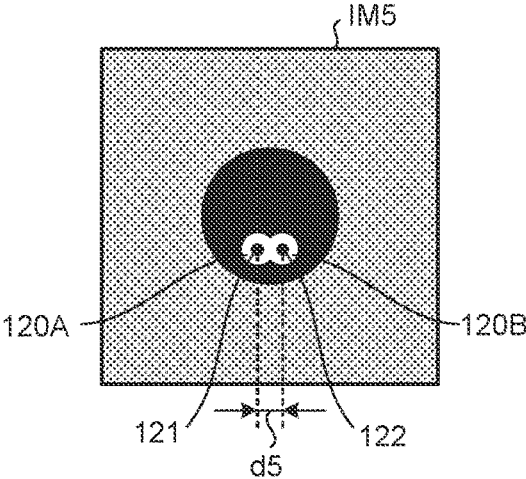
FIG. 14 is a diagram illustrating an example of the image data on the eyeball that is captured with the first light source and the second light source being turned on at the same timing.

FIGS. 12 to 14 are diagrams illustrating examples of image data on the eyeball EB that is captured with the first light source 21A and the second light source 21B being turned on at the same timing. FIG. 12 illustrates the example in which an object distance x between the imaging unit 22 and the subject is similar to that in FIG. 7. FIG. 13 illustrates an example of the case where an object distance x is shorter than that in the state in FIG. 12. FIG. 14 illustrates an example of the case where the object distance is much shorter than that in the state in FIG. 13. In FIGS. 12 to 14, the first cornea reflection center 121 and the second cornea reflection center 122 are presented in black dots for easy determination of their positions; however, there are no black points actually.

In image data IM3 and IM4 illustrated in FIGS. 12 and 13, the image of the first cornea reflection image 120A and the image of the second cornea reflection image 120B are separated from each other. In this case, the position calculator 32 is able to calculate the image of the first cornea reflection image 120A and the image of the second cornea reflection image 120B as separate high-luminance areas and calculate sets of coordinates of luminance gravity centers of the separate high-luminance areas independently. Accordingly, it is possible to calculate positions of the first cornea reflection center 121 and the second cornea reflection center 122 separately from the single set of image data IM3 or IM4 and calculate center-center distances d3 or d4.

On the other hand, in image data IM5 illustrated in FIG. 14, the image of the first cornea reflection image 120A and the image of the second cornea reflection image 120B are joined partly. In this state, the position calculator 32 has difficulties in calculating the image of the first cornea reflection image 120A and the image of the second cornea reflection image 120B as separate high-luminance areas. Accordingly, in such a case, using the image data IM1 and IM2 obtained by capturing the images of the eyeball EB with the first light source 21A and the second light source 21B being turned on at different sets of timing makes it possible to calculate the positions of the first cornea reflection center 121 and the second cornea reflection center 122 assuredly and calculate a center-center distance d5.

INDUSTRIAL APPLICABILITY

The distance calculation device, the distance calculation method, and the distance calculation program according to the disclosure are usable for, for example, a processing device, such as a computer, or the like.

REFERENCE SIGNS LIST

EB EYEBALL, d, d1, d2, d3, d4, d5 CENTER-CENTER DISTANCE, IM1, IM2, IM3, IM4, IM5 IMAGE

DATA, r CORNEA CURVATURE RADIUS, X OBJECT DISTANCE, 10 DISPLAY DEVICE, 11 DISPLAY UNIT, 20 IMAGE ACQUISITION DEVICE, 21 LIGHT SOURCE UNIT, 21A FIRST LIGHT SOURCE, 21B SECOND LIGHT SOURCE, 21C VIRTUAL LIGHT SOURCE, 22 IMAGING UNIT, 30 COMPUTER SYSTEM, 30A ARITHMETIC PROCESSING UNIT, 30B STORAGE DEVICE, 30C COMPUTER PROGRAM, 31 IMAGING CONTROLLER, 32 POSITION CALCULATOR, 33 CENTER-CENTER DISTANCE CALCULATOR, 34 OBJECT DISTANCE CALCULATOR, 35 DETECTION PROCESSOR, 36 STORAGE UNIT, 40 OUTPUT DEVICE, 50 INPUT DEVICE, 60 INPUT-OUTPUT INTERFACE DEVICE, 80 DISTANCE CALCULATION DEVICE, 100 LINE-OF-SIGHT DETECTION DEVICE, 110 CORNEA CURVATURE CENTER, 112 PUPIL, 112C PUPIL CENTER, 113C, 121, 122, 124 CORNEA REFLECTION CENTER, 120A FIRST CORNEA REFLECTION IMAGE, 120B SECOND CORNEA REFLECTION IMAGE, 121 FIRST CORNEA REFLECTION CENTER, 122 SECOND CORNEA REFLECTION CENTER

What is claimed is:

1. A distance calculation device comprising:
   a first light source and a second light source that emit detection light from positions different from each other and that apply the detection light to an eyeball of a subject;
   an imaging unit that captures an image of the eyeball to which the detection light is applied;
   a position calculator that, based on the image of the eyeball, calculates a position of a first cornea reflection center according to the detection light from the first light source and a position of a second cornea reflection center according to the detection light from the second light source;
   a center distance calculator that calculates a center-center distance between the position of the first cornea reflection center and the second cornea reflection center based on a number of pixels between the position of the first cornea reflection center and the position of the second cornea reflection center of the image of the eyeball; and
   an object distance calculator that sets a given constant for a cornea curvature radius of the eyeball, and based on the center-center distance and the cornea curvature radius of the eyeball of the subject, calculates an object distance between the imaging unit and the eyeball,
   wherein the first light source and the second light source emit the detection light alternately, and the position calculator calculates the position of the first cornea reflection center and the position of the second cornea reflection center based on images captured at respective timings of emission.

2. The distance calculation device according to claim 1, wherein
   the position calculator calculates the position of the first cornea reflection center based on a first image, of the images, that is captured at a timing at which the detection light is emitted from the first light source and calculates the position of the second cornea reflection center based on a second image, of the images, that is captured at a timing at which the detection light is emitted from the second light source.

3. A distance calculation method comprising:

emitting detection light from a first light source and a second light source that are arranged in positions different from each other and applying the detection light to an eyeball of a subject, wherein the emitting comprises emitting the detection light from the first light source and the second light source alternately;

by an imaging unit, capturing, at respective different timings of emission from the first light source and the second light source, images of the eyeball to which the detection light is applied;

based on the images of the eyeball captured at the respective different timings of emission, calculating a position of a first cornea reflection center according to the detection light from the first light source and a position of a second cornea reflection center according to the detection light from the second light source;

calculating a center-center distance between the first cornea reflection center and the second cornea reflection center based on a number of pixels between the position of the first cornea reflection center and the position of the second cornea reflection center of the image of the eyeball;

setting a given constant for a cornea curvature radius of the eyeball; and based on the center-center distance and the cornea curvature radius of the eyeball, calculating an object distance between the imaging unit and the eyeball.

4. A non-transitory computer readable recording medium storing therein a distance calculation program that causes a computer to execute a process of emitting detection light alternately from a first light source and a second light source that are arranged in positions different from each other and applying the detection light to an eyeball of a subject;

a process of, by an imaging unit, capturing images of the eyeball to which the detection light is applied at respective different timings of emission from the first light source and the second light source;

a process of, based on the images of the eyeball captured at the respective different timings of emission, calculating each of a position of a first cornea reflection center according to the detection light from the first light source and a position of a second cornea reflection center according to the detection light from the second light source;

a process of calculating a center-center distance between the first cornea reflection center and the second cornea reflection center based on a number of pixels between the first cornea reflection center and the second cornea reflection center of the image of the eyeball;

a process of setting a given constant for a cornea curvature radius of the eyeball; and a process of, based on the center-center distance and the cornea curvature radius of the eyeball, calculating an object distance between the imaging unit and the eyeball.

* * * * *